(12) United States Patent
Bauer

(10) Patent No.: US 7,371,913 B2
(45) Date of Patent: May 13, 2008

(54) SELECTIVE AROMATICS ISOMERIZATION PROCESS

(75) Inventor: John E. Bauer, LaGrange Park, IL (US)

(73) Assignee: UOP LLC, Des Plaines, IL (US)

( * ) Notice: Subject to any disclaimer, the term of this patent is extended or adjusted under 35 U.S.C. 154(b) by 317 days.

(21) Appl. No.: 11/171,983

(22) Filed: Jun. 30, 2005

(65) Prior Publication Data

US 2007/0004948 A1 Jan. 4, 2007

(51) Int. Cl.
*C07C 5/27* (2006.01)
(52) U.S. Cl. .................................... 585/481
(58) Field of Classification Search ............. 585/481
See application file for complete search history.

(56) References Cited

U.S. PATENT DOCUMENTS

| | | | |
|---|---|---|---|
| 3,201,491 A | 8/1965 | Stine et al. ............. 260/676 |
| 3,377,400 A | 4/1968 | Wise ....................... 260/668 |
| 3,626,020 A | 12/1971 | Neuzil ................ 260/674 SA |
| 3,696,107 A | 10/1972 | Neuzil ................ 260/674 SA |
| 3,856,872 A | 12/1974 | Morrison ............. 260/668 A |
| 4,039,599 A | 8/1977 | Gewartowski ....... 260/668 A |
| 4,159,282 A | 6/1979 | Olson et al. ............. 585/481 |
| 4,163,018 A | 7/1979 | Tada et al. ............ 260/429.9 |
| 4,184,943 A | 1/1980 | Anderson ............ 208/310 R |
| 4,278,565 A | 7/1981 | Chen et al. ............ 252/455 Z |
| 4,381,419 A | 4/1983 | Wylie ...................... 585/828 |
| 4,402,832 A | 9/1983 | Gerhold ................... 210/659 |
| 4,957,891 A | 9/1990 | Sachtler et al. ............ 502/61 |
| 4,962,258 A | 10/1990 | Amelse et al. ........... 585/480 |
| 5,240,891 A | 8/1993 | Patton et al. ............... 502/66 |
| 6,872,866 B1 | 3/2005 | Nemeth et al. ........... 585/481 |

*Primary Examiner*—Thuan Dinh Dang
(74) *Attorney, Agent, or Firm*—Maryann Maas

(57) ABSTRACT

A process for isomerizing xylenes while retaining ethylbenzene in a $C_8$-aromatics stream in liquid phase uses a gallium-substituted pentasil zeolite in the absence of hydrogen.

10 Claims, No Drawings

SELECTIVE AROMATICS ISOMERIZATION PROCESS

FIELD OF THE INVENTION

This invention relates to catalytic hydrocarbon conversion, and more specifically to aromatics isomerization.

GENERAL BACKGROUND AND RELATED ART

The xylene isomers are important intermediates which find wide and varied application in chemical syntheses. Para-xylene is a feedstock for terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

The proportions of xylene isomers obtained from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Various catalysts and processes have been developed to effect xylene isomerization, and these usually are differentiated by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function.

Catalysts containing molecular sieves have become prominent in these approaches to xylene isomerization in the past few decades. U.S. Pat. No. 3,377,400 teaches liquid-phase isomerization and disproportionation of alkylaromatic hydrocarbons using a crystalline aluminosilicate catalyst. U.S. Pat. No. 3,856,872 teaches xylene isomerization and ethylbenzene conversion with a catalyst containing ZSM-5, -12, or -21 zeolite. U.S. Pat. No. 4,957,891 discloses a catalyst for the isomerization of a mixture of xylenes and ethylbenzene comprising a platinum-group metal, gallium-substituted pentasil zeolite and zirconia-alumina matrix. U.S. Pat. No. 4,962,258 discloses a process for isomerization of a major amount of xylenes and minor amount of ethylbenzene over gallium-containing, crystalline silicate molecular sieves as an improvement over aluminosilicate zeolites ZSM-5, ZSM-12, and ZSM-21. U.S. Pat. No. 6,872,866 discloses a liquid-phase process using two catalysts comprising beta zeolite and low $Si/Al_2$ MTW for the isomerization of xylenes and ethylbenzene.

In contrast to the known art for isomerizing xylenes with effective conversion of ethylbenzene, the present invention features high retention of ethylbenzene while isomerizing xylenes. This approach enables effective further processing of the isomerized product with selective conversion of ethylbenzene to paraxylene. Alternatively, the product from the present process could be separated to recover ethylbenzene as well as para-xylene and/or other xylene isomers. In yet other embodiments, ethylaromatics can be preserved when isomerizing alkylaromatic feed mixtures containing higher alkylaromatics such as ethyltoluene.

SUMMARY OF THE INVENTION

A principal object of the present invention is to provide a novel process using a combination of catalysts and systems tailored to specific reactions for isomerization of $C_8$-aromatic hydrocarbons to obtain improved yields of desired xylene isomers with high retention of ethylbenzene and concomitant preservation of $C_8$ cyclics.

A broad embodiment of the invention is a process for the isomerization of a non-equilibrium alkylaromatic feed mixture comprising a substantial content of one or more ethylaromatic hydrocarbons by contacting the feed mixture in liquid phase with an isomerization catalyst, comprising Ga-MFI zeolite and having the substantial absence of a platinum-group metal, at isomerization conditions in the substantial absence of hydrogen to obtain an isomerized product comprising a higher concentration of at least one alkylaromatic isomer with a conversion of the ethylaromatic hydrocarbons of no more than about 7%.

A more specific embodiment of the invention is a process for the isomerization of a non-equilibrium $C_8$-aromatic feed mixture comprising a substantial content of ethylbenzene by contacting the feed mixture in liquid phase with an isomerization catalyst, comprising gallium-substituted pentasil zeolite and having the substantial absence of a platinum-group metal, at isomerization conditions in the substantial absence of hydrogen to obtain an isomerized product comprising a higher concentration of at least one xylene isomer with a conversion of ethylbenzene of no more than about 7%.

A yet more specific embodiment of the invention is a process for the isomerization of a non-equilibrium $C_8$-aromatic feed mixture comprising a substantial content of ethylbenzene by contacting the feed mixture in liquid phase with an isomerization catalyst, comprising a gallium-substituted pentasil zeolite and having the substantial absence of a platinum-group metal, at isomerization conditions in the substantial absence of hydrogen to obtain an isomerized product comprising a higher concentration of at least one xylene isomer with a conversion of ethylbenzene of no more than about 7%.

These and other objects and embodiments will become evident from the following detailed description of the invention.

DETAILED DESCRIPTION OF THE INVENTION

The non-equilibrium alkylaromatic feed mixture to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination suitable for isomerization to obtain at least one more valuable alkylaromatic isomer in an isomerized product. The feed mixture comprises a substantial content of one or more ethylaromatic hydrocarbons containing at least one ethyl group, i.e., at least one R of at least one of the alkylaromatic hydrocarbons is $C_2H_5$. Suitable components of the feed mixture generally include, for example but without so limiting the invention, ethylbenzene, meta-xylene, ortho-xylene, para-xylene, ethyl-toluenes, trimethylbenzenes, diethyl-benzenes, triethylbenzenes, methylpropylbenzenes, ethylpropylbenzenes, diisopropylbenzenes, and mixtures thereof.

Isomerization of a non-equilibrium $C_8$-aromatic feed mixture comprising xylenes and ethylbenzene is a particularly preferred application of the present invention. By "non-equilibrium" is meant that at least one $C_8$-aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from one or more aromatics-production or aromatics-conversion processes. The feed mixture generally has an ortho-xylene content in the approximate range of 0 to 35 wt-%, a meta-xylene content in the approximate range of 20 to 95 wt-% and a para-xylene content in the approximate range of 0 to 30 wt-% with a substantial content of ethylbenzene.

Although the present process may be used advantageously for the isomerization of an ethylbenzene-free mixture of xylenes, the feed mixture thus generally will have a substantial content of ethylbenzene. The term "substantial content" generally relates to an ethylbenzene content of at least from about 1 to about 60 wt-%, and more usually of from about 5 to about 35 wt-%. Often the ethylbenzene content is at about 10 wt-% or more, and sometimes at least about 15wt-%.

The alkylaromatic feed mixture may be derived from any of a variety of original sources, e.g., petroleum refining, thermal or catalytic cracking of hydrocarbons, coking of coal, or petrochemical conversions. Preferably the feed mixture utilized in the present invention is found in appropriate fractions from various petroleum-refinery streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 wt-%. Preferably the isomerizable hydrocarbons consist essentially of aromatics, however, to ensure pure products from downstream recovery processes.

According to the process of the present invention, an alkylaromatic hydrocarbon feed mixture is contacted with a catalyst of the type hereinafter described in liquid phase. Contacting may be effected using the catalyst system in a fixed-bed system, a moving-bed system, a fluidized-bed system, slurry system or ebullated-bed system or in a batch-type operation. In view of the danger of attrition loss of valuable catalysts and of the simpler operation, it is preferred to use a fixed-bed system.

In the preferred manner, the feed mixture is preheated by suitable heating means as known in the art to the desired reaction temperature and passes in liquid phase in the substantial absence of hydrogen into a reactor section containing a fixed bed or beds of the isomerization catalyst. The term "substantial absence of hydrogen" means that no free hydrogen is added to the feed mixture and that any dissolved hydrogen from prior processing is substantially less than 0.05 moles/mole of feed, frequently less than 0.01 moles/mole, and possibly not detectable by usual analytical means. The reactor section may comprise a single reactor or two or more separate reactors with suitable means therebetween to ensure that the desired isomerization temperature is maintained at the entrance to each reactor. The reactants may be contacted with the catalyst bed in upward-, downward-, or radial-flow fashion to obtain an isomerized product which contains alkylaromatic isomers in a ratio which differs from that of the feed mixture. In the preferred processing of $C_8$-aromatics, the isomerized product contains xylenes in proportions closer to equilibrium than in the feed mixture plus ethylbenzene in a proportion relating to that in the feed mixture.

The present process features high retention of ethylaromatics, and specifically of ethylbenzene, through the isomerization process. Conversion of ethylaromatics and specifically of ethylbenzene, relating the amount in the isomerized product to the amount in the feed mixture, is usually no more than about 7%, preferably less than about 5%, and often less than about 3%.

The alkylaromatic feed mixture, preferably a non-equilibrium mixture of $C_8$ aromatics, contacts the isomerization catalyst in liquid phase at suitable isomerization conditions. Such conditions comprise temperature ranging from about 1000 to about 500° C., and preferably from about 200° to 400° C. The pressure is sufficient to maintain the feed mixture in liquid phase, generally from about 500 kPa to 5 MPa absolute. The reactor section contains a sufficient volume of catalyst to provide a liquid hourly space velocity with respect to the feed mixture of from about 0.5 to 50 $hr^{-1}$, and preferably 0.5 to 20 $hr^{-1}$.

The isomerized product comprises a concentration of at least one alkylaromatic isomer that is higher than the equilibrium concentration at isomerization conditions. The isomerized product preferably is a mixture of $C_8$ aromatics having a concentration of para-xylene that is higher than that of the feed with high retention of ethylbenzene. Preferably the concentration of para-xylene is at least 22 wt-%, and often is about 23 wt-% or more. The $C_8$-aromatic ring loss relative to the feed mixture is usually less than about 3 wt-% and often less than about 2 wt-%.

The specific further processing of the isomerized product is not deemed to be critical to the instant invention. Typically, reactor effluent is condensed and the liquid product then is fractionated to remove light and/or heavy byproducts and obtain the isomerized product. In some instances, certain product species such as ortho-xylene may be recovered from the isomerized product by selective fractionation. The isomerized product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in, for example, U.S. Pat. No. 3,626,020; U.S. Pat. No. 3,696,107; U.S. Pat. No. 4,039,599; U.S. Pat. No. 4,184,943; U.S. Pat. No. 4,381,419 and U.S. Pat. No. 4,402,832, incorporated herein by reference thereto.

An advantageous further processing step is the selective conversion of ethylbenzene to para-xylene, exemplified in U.S. Pat. No. 5,240,891 which discloses a MgAPSO molecular sieve having a narrow ratio of framework magnesium and its use in xylene isomerization. This processing step may be applied to the isomerized product either without or after one or more of the separation steps described above. The combination of the present invention with selective ethylbenzene conversion can yield a product having a superequilibrium concentration of para-xylene.

The catalyst used in the processes of this invention comprises a gallium-substituted pentasil zeolite utilized in the instant invention preferably has a formula (expressed in terms of mole ratios of oxides) as follows:

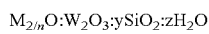

$$M_{2/n}O:W_2O_3:ySiO_2:zH_2O$$

wherein M is at least one cation of valence n, W is gallium and/or aluminum, y is at least 5, preferably at least 12, and z is from 0 to 40. The zeolite preferably has an X-ray diffraction characteristic of pentasil zeolites, which includes ZSM-5, ZSM-8, ZSM-11, ZSM-12, ZSM-23, and ZSM-35, with ZSM-5, often characterized as MFl, being particularly preferred. "Pentasil" is a term used to describe a class of shape-selective zeolites. This novel class of zeolites is well known to the art and is typically characterized by a silica/alumina mole ratio of at least about 12. Suitable descriptions of the pentasils may be found in U.S. Pat. No. 4,159,282; U.S. Pat. No. 4,163,018; and U.S. Pat. No. 4,278,565, all of which are incorporated herein by reference. The zeolite framework may contain only gallium and silicon atoms or may contain a combination of gallium, aluminum, and silicon atoms. The gallium content, expressed as mole ratios of $SiO_2/Ga_2O_3$, may range from 20:1 to 400:1. The preferred gallium-substituted pentasil zeolite has a ZSM-5 or MFl structure with a gallium content ranging from 0.1 to 10 wt-% of the zeolite, more preferably ranging from about 0.5 to 5 wt-% and most preferably at least about 1 wt-%. The gallium-substituted pentasil zeolite may be prepared by crystallization from a reaction mixture comprising a silica source, a source of $Ga_2O_3$, a source of $Al_2O_3$ if desired, and optionally an organic template compound. It is believed that the preparation of zeolites is within the competence of one skilled in the art and a particular preparation method is not critical to the instant invention. The preferred zeolite component of the present catalyst, gallium-substituted ZSM-5 or MFl, is referred to herein as Ga-MFl.

The Ga-MFl zeolite preferably is composited with a binder for convenient formation of catalyst particles. The proportion of zeolite in the catalyst may range from about 1 to about 99 wt-%, and is often about 5 to about 90 wt-%, and preferably about 20 to about 80 wt-%, the remainder principally being the binder component. Refractory inorganic oxide binders are preferred and the binder should be a porous, adsorptive support having a surface area of about 25 to about 500 m²/g. Suitable binder materials include those which have traditionally been used in hydrocarbon conversion catalysts such as: (1) refractory inorganic oxides such as aluminas, zirconia, titania, chromia, zinc oxide, magnesia, thoria, boria, silica-alumina, silica-magnesia, chromia-alumina, alumina-boria, silica-zirconia, phosphorus-alumina, etc.; (2) ceramics, porcelain, bauxite; (3) silicas or silica gel, silicon carbide, clays and silicates including those synthetically prepared and naturally occurring, which may or may not be acid treated, for example, attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO\ Al_2O_3$ where M is a metal having a valence of 2; and (6) combinations of materials from one or more of these groups.

A zirconia-alumina matrix is particularly preferred. This matrix is a composite of two porous refractory inorganic oxides having basic chemical formulae of $ZrO_2$ and $Al_2O_3$, respectively. Suitable alumina materials are the crystalline aluminas known as gamma-, eta-, and theta-, with gamma- or eta-alumina being the most preferred. It is preferred that the matrix contains from about 90 to about 99 wt-% alumina. The zirconia portion of the matrix preferably constitutes from about 1 to about 10 wt-% of the matrix. Preferred physical properties of the matrix include an apparent bulk density of 0.3 to about 0.8 g/cc and surface area characteristics such that the average pore diameter is about 20 to 300 angstroms, the pore volume is about 0.1 to about 1 cc/g, and the surface area is about 100 to 500 m²/g.

Preparation of the matrix material may be performed in any suitable manner known to the art. A particularly preferred method of preparing the zirconia-alumina matrix is believed to result in a finished catalyst that exhibits superior performance when utilized for the conversion of hydrocarbons. This preferred method involves cogelation of zirconia and alumina in an intimate admixture with the gallium-substituted pentasil zeolite. The first step in the preparation method involves the formation of an alumina hydrosol. Any technique known to the art may be utilized to prepare the alumina hydrosol, however, a preferred method involves reacting aluminum metal with hydrochloric acid. The gallium-substituted pentasil zeolite is then added to the alumina hydrosol to form a homogeneous mixture. To the alumina sol and zeolite mixture is added a zirconia sol, for example, zirconium oxychloride, and to the resultant mixture is added a suitable gelling agent, such as, hexamethylenetetramine. It is believed that the order of combining the alumina sol, zirconia sol, zeolite, and gelling agent is unimportant. Therefore, any combination sequence of the ingredients should produce the catalyst of the instant invention. Once gelled, the composite may be formed into any desired shape such as spheres, pills, cakes, extrudates, powders, granules, tablets, etc. and utilized in any desired size. In a preferred embodiment, the resultant mixture is first shaped in the form of a sphere and then gelled.

A spherical catalyst suitably is manufactured by the well-known oil drop method. Preparation of the preferred spheres generally involves continuously dropping a mixture of molecular sieve, zirconia-alumina sol, and gelling agent into an oil bath maintained at elevated temperatures. Alternatively, gelation of an alumina sol or silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents that may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

Another suitable shape for the catalyst composite is an extrudate. The well-known extrusion method initially involves mixing of the molecular sieve with optionally the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from about 30 to about 50 wt-% being preferred. The dough is then extruded through a die pierced with multiple holes and the spaghetti-shaped extrudate is cut to form particles in accordance with techniques well known in the art. A multitude of different extrudate shapes is possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

Preferably, the resulting composite then is washed and dried at a relatively low temperature of about 50° to 200° C. and subjected to a calcination procedure at a temperature of about 450° to 700° C. for a period of about 1 to about 20 hours.

The catalyst optionally is subjected to steaming to tailor its acid activity. The steaming may be effected at any stage of the zeolite treatment. Steaming conditions comprise a water concentration of about 5 to 100 vol-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed.

It is a feature of the invention that the catalyst is free of an added metal component, and particularly free of a costly platinum-group metal.

The catalysts of the present invention may contain a halogen component, comprising either fluorine, chlorine, bromine or iodine or mixtures thereof, with chlorine being preferred. Preferably, however, the catalyst contains no added halogen other than that associated with other catalyst components.

The catalyst composite is dried at a temperature of from about 100° to about 320° C. for a period of from about 2 to about 24 or more hours and, usually, calcined at a temperature of from about 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The following examples are presented only to illustrate certain specific embodiments of the invention, and should not be construed to limit the scope of the invention as set forth in the claims. There are many possible other variations within the spirit of the invention, as those of ordinary skill in the art will recognize.

EXAMPLE I

A catalyst of the invention was prepared in accordance with the teachings of U.S. Pat. No. 4,957,891. A quantity of gallium-substituted pentasil zeolite having an X-ray diffraction pattern equivalent to that of MFI/ZSM-5 was prepared by adding a silica source, Ludox HS-40, to an aqueous solution containing an organic template, tetrapropylammonium bromide. The weight ratio of silica to template was about 4.9:1. A solution of sodium gallate was added to the silica and template mixture in an amount to give about 2 wt-% gallium based on the finished zeolite. The resultant mixture was autoclaved at about 125° C. for approximately 72 hours. The zeolite obtained was washed, filtered and dried to yield a gallium-substituted pentasil zeolite (Ga-MFI) containing approximately 3 wt-% gallium.

A portion of the zeolite described above was mixed with alumina hydrosol, prepared by digesting metallic aluminum in hydrochloric acid, to yield a zeolite content in the finished catalyst equal to about 50 wt-%. To this mixture was added enough zirconium oxychloride sol, containing approximately 20 wt-% $ZrO_2$, such that the finished zeolite zirconia-alumina composite contained approximately 5 wt-% $ZrO_2$. Finally, a solution of hexamethylenetetramine was added as a gelling agent. The final mixture was dispersed as droplets into an oil bath at a temperature of about 95° C. The droplets remained in the oil bath until they formed hydrogel spheres. The spheres were removed from the oil bath and washed with an aqueous solution containing about 0.5 wt-% ammonia. The spheres were then air dried at 110° C. for about 12 hours and then calcined in air at a temperature of about 650° C. After calcination, the composite was washed with 0.5% $NH_3/H_2O$ solution at 95° C. and then oven-dried at 110° C. No platinum or sulfur was added to the catalyst which was designated Catalyst A.

EXAMPLE II

Catalyst B was prepared in the same manner as Catalyst A, except that the content of gallium in the GaMFI zeolite was about 2.5 wt-%

EXAMPLE III

Catalyst C was prepared in the same manner as Catalyst A, except that the content of gallium in the GaMFI zeolite was about 1.5 wt-%.

EXAMPLE IV

Catalyst D was prepared in the same manner as Catalyst A, except that the content of gallium in the GaMFI zeolite was about 0.7 wt-%

EXAMPLE V

Catalyst A was evaluated for xylene isomerization and ethyl-benzene retention using a pilot plant flow reactor processing a non-equilibrium $C_8$ aromatic feed having the following approximate composition in wt-%:

| | |
|---|---|
| Toluene | 1.2 |
| $C_8$ Non-aromatics | 6.3 |
| Ethylbenzene | 13.9 |
| Para-xylene | 0.8 |
| Meta-xylene | 55.6 |
| Ortho-xylene | 22.2 |

EXAMPLE VI

Pilot-plant test conditions and results are as follows. The above feed contacted the Catalyst at a pressure of 3.5 MPa in the liquid phase. A range of process conditions (WHSV=weight hourly space velocity) and the resulting performance measures are shown below for Catalyst A:

|  | Temperature ° C. | | | |
| --- | --- | --- | --- | --- |
|  | 280 | 280 | 300 | 300 |
| WHSV, hr$^{-1}$ | 2.3 | 4.5 | 8.7 | 13.0 |
| p-xylene/xylenes, wt-% | 23.8 | 22.7 | 23.6 | 22.9 |
| C$_8$ ring loss, wt-% | 1.1 | 0.4 | 0.9 | 0.6 |
| EB conversion, % | 4.2 | 2.0 | 4.5 | 2.3 |

Note that the "C$_8$ ring loss" is in mol-% defined as "(1-(C$_8$ naphthenes and aromatics in product)/(C$_8$ naphthenes and aromatics in feed))*100", which represents material that has to be circulated to another unit in an aromatics complex. Such circulation is expensive and a low amount of C$_8$ ring loss is preferred. Ethylbenzene conversion, 2 to 4.5%, as well as ring loss was low in all cases.

What is claimed is:

1. A process for the isomerization of a non-equilibrium alkylaromatic feed mixture comprising a substantial content of one or more ethylaromatic hydrocarbons by contacting the feed mixture in liquid phase with an isomerization catalyst, comprising a zirconia-alumina matrix and a gallium-substituted pentasil zeolite and having the substantial absence of a platinum-group metal, at isomerization conditions in the substantial absence of hydrogen to obtain an isomerized product comprising a higher concentration of at least one alkylaromatic isomer with a conversion of the ethylaromatic hydrocarbons of less than about 5% and a C$_8$-aromatic ring loss relative to the feed mixture of less than about 2 wt-%.

2. The process of claim 1 wherein the isomerization conditions comprise a temperature of from about 100° to about 500° C., a pressure of from about 500 kPa to 5 MPa and a liquid hourly space velocity of from about 0.5 to 50 hr$^{-1}$.

3. A process for the isomerization of a non-equilibrium C$_8$-aromatic feed mixture comprising a substantial content of ethylbenzene by contacting the feed mixture in liquid phase with an isomerization catalyst, comprising a zirconia-alumina matrix and a gallium-substituted pentasil zeolite and having the substantial absence of a platinum- group metal, at isomerization conditions in the substantial absence of hydrogen to obtain an isomerized product comprising a higher concentration of at least one xylene isomer with a conversion of ethylbenzene of less than about 5% and a C$_8$-aromatic ring loss relative to the feed mixture of less than about 2 wt-%.

4. The process of claim 3 wherein the ethylbenzene content of the feed stream is from about 5 to about 35 wt-%.

5. The process of claim 4 wherein the ethylbenzene content of the feed stream is about 10 wt-% or more.

6. The process of claim 3 wherein the isomerization conditions comprise a temperature of from about 100° to about 500° C., a pressure of from about 500 kPa to 5 MPa and a liquid hourly space velocity of from about 0.5 to 50 hr$^{-1}$.

7. A process for the isomerization of a non-equilibrium C$_8$-aromatic feed mixture comprising a substantial content of ethylbenzene by contacting the feed mixture in liquid phase with an isomerization catalyst, comprising a Ga-MFI zeolite and a zirconia-alumina matrix and having the substantial absence of a platinum-group metal, at isomerization conditions in the substantial absence of hydrogen to obtain an isomerized product comprising a higher concentration of at least one xylene isomer with a conversion of ethylbenzene of less than about 5% and a C$_8$-aromatic ring loss relative to the feed mixture of less than about 2 wt-%.

8. The process of claim 7 wherein the ethylbenzene content of the feed stream is from about 5 to about 35 wt-%.

9. The process of claim 8 wherein the ethylbenzene content of the feed stream is about 10 wt-% or more.

10. The process of claim 7 wherein the isomerization conditions comprise a temperature of from about 100° to about 500° C., a pressure of from about 500 kPa to 5 MPa and a liquid hourly space velocity of from about 0.5 to 50 hr$^{-1}$.

* * * * *